(12) United States Patent
Clarke et al.

(10) Patent No.: US 7,723,056 B1
(45) Date of Patent: May 25, 2010

(54) PARTICLES

(75) Inventors: David J. Clarke, Sandbach (GB);
Michael H. Harrison, Glossop (GB);
Harmesh S. Aojula, Saddleworth (GB)

(73) Assignee: The University of Manchester, Manchester (GB)

( * ) Notice: Subject to any disclaimer, the term of this patent is extended or adjusted under 35 U.S.C. 154(b) by 0 days.

(21) Appl. No.: 09/529,342

(22) PCT Filed: Oct. 14, 1998

(86) PCT No.: PCT/GB98/03071

§ 371 (c)(1),
(2), (4) Date: Jul. 27, 2000

(87) PCT Pub. No.: WO99/20252

PCT Pub. Date: Apr. 29, 1999

(30) Foreign Application Priority Data

Oct. 16, 1997 (GB) .................................. 9721901.8

(51) Int. Cl.
*G01N 33/554* (2006.01)

(52) U.S. Cl. ...................... 435/7.32; 436/518; 436/829; 424/450

(58) Field of Classification Search .................. 264/4.3; 424/417, 1.21, 48, 486, 600, 932; 435/288.3, 435/10, 325, 182, 188, 810, 177, 180; 436/518, 436/10; 422/55, 82.1, 58; 514/2, 12–14, 514/16, 17, 18; 530/324, 402
See application file for complete search history.

(56) References Cited

U.S. PATENT DOCUMENTS

| | | | |
|---|---|---|---|
| 4,342,826 A * | 8/1982 | Cole ........................... 435/7.9 |
| 4,603,044 A | 7/1986 | Geho et al. |
| 4,808,517 A * | 2/1989 | Blondin et al. ................. 435/4 |
| 4,829,011 A * | 5/1989 | Gibbons ..................... 436/512 |
| 4,885,172 A * | 12/1989 | Bally et al. .................. 424/417 |
| 4,900,556 A | 2/1990 | Wheatley et al. |
| 4,948,590 A | 8/1990 | Hawrot et al. |
| 5,047,245 A * | 9/1991 | Bally et al. .................. 424/450 |
| 5,108,921 A | 4/1992 | Low et al. |
| 5,258,284 A * | 11/1993 | Morris et al. .................. 435/6 |
| 5,334,761 A | 8/1994 | Gebeyehu et al. |

(Continued)

FOREIGN PATENT DOCUMENTS

DE 39 35 257 4/1991

(Continued)

OTHER PUBLICATIONS

Rizzo et al, Alamethicin incorporation in lipid bilayers: a thermodynamic study, 1987, Biochemistry, 26, 2751-2759.*

(Continued)

*Primary Examiner*—Nelson Yang
(74) *Attorney, Agent, or Firm*—Nixon & Vanderhye PC.

(57) ABSTRACT

Lipid vesicle particles capable of being targeted to a cell type of interest, said particle incorporating a peptide which is responsive to a predetermined metabolic signal from the targeted cell so as to modulate the permeability of the particle, said particle further incorporating a species to be targeted to the cell which is activated on said modulation of permeability. The particles may be used in methods for detecting cells, methods of treating cells and also therapeutically.

32 Claims, 3 Drawing Sheets

U.S. PATENT DOCUMENTS

| | | | |
|---|---|---|---|
| 5,374,548 A | | 12/1994 | Caras |
| 5,416,016 A | | 5/1995 | Low et al. |
| 5,494,803 A | * | 2/1996 | Carbonell et al. .......... 435/7.92 |
| 5,512,294 A | | 4/1996 | Li et al. |
| 5,525,232 A | | 6/1996 | Veiro et al. |
| 5,552,311 A | | 9/1996 | Sorscher et al. |
| 5,618,916 A | | 4/1997 | Ratliff et al. |
| 5,635,382 A | | 6/1997 | Low et al. |
| 5,688,488 A | | 11/1997 | Low et al. |
| 5,776,487 A | * | 7/1998 | Maxfield Wilson et al. . 424/450 |
| 5,780,319 A | * | 7/1998 | Maxfield Wilson et al. . 436/518 |
| 5,824,490 A | * | 10/1998 | Coffey et al. .............. 435/7.23 |
| 5,874,104 A | * | 2/1999 | Adler-Moore et al. ....... 424/450 |
| 5,994,149 A | * | 11/1999 | Robinson et al. ............ 436/518 |
| 6,020,142 A | * | 2/2000 | Levinson et al. ............. 435/7.1 |
| 6,087,325 A | * | 7/2000 | Meers et al. .................... 514/2 |
| 6,132,764 A | * | 10/2000 | Li et al. ....................... 424/450 |
| 6,344,436 B1 | * | 2/2002 | Smith et al. ..................... 514/2 |
| 6,417,326 B1 | * | 7/2002 | Cullis et al. ................. 530/324 |
| 6,468,558 B2 | * | 10/2002 | Wong .......................... 424/450 |
| 6,482,586 B1 | * | 11/2002 | Arab et al. ...................... 435/4 |
| 6,627,652 B1 | * | 9/2003 | Chandraratna .............. 514/448 |

FOREIGN PATENT DOCUMENTS

| | | |
|---|---|---|
| EP | 0 298 280 | 1/1989 |
| EP | 0 393 707 A | 10/1990 |
| WO | WO 90/12096 | 10/1990 |
| WO | WO 91/04014 | 4/1991 |
| WO | WO 93 25225 A | 12/1993 |
| WO | WO 94/05624 | 3/1994 |
| WO | WO 96 40060 A | 12/1996 |
| WO | WO 98 16240 A | 4/1998 |

OTHER PUBLICATIONS

Wyman et al, Design, synthesis, and characterization of a cationic peptide that binds to nucleic acids and permeabilizes bilayers, Mar. 1997, Biochemistry, 36, 30008-30017.*

Parente et al, Mechanism of leakage of phospholipid vesicle contents induced by the peptide GALA, 1990, Biochemistry, 29, 8720-8728.*

Leippe t al, Pore forming peptide of pathogenic Entamoeba histolytica, 1991, Proc Natl Acad Sci, 88, 7658-7663.*

Trubetskaya et al, Monoclonal antibody to human endothelial cell surface internalization and liposome delivery in cell culture, 1988, FEBS letters, 228, 131-134.*

Matsuzaki, et al, Pore formation and translocation of melittin, Aug. 1997, Biophys J, 73, 831-838.*

Subbarao et al., pH dependent bilayer destabilization by an amphiphathic peptide, 1987, 26, 2964-2972.*

* cited by examiner

SEQUENCE LISTING

<160> NUMBER OF SEQ ID NOS: 1

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: N, Myrstic-GALA

```
<400> SEQUENCE: 1

Trp Glu Ala Ala Leu Ala Glu Ala Leu Ala Glu Ala Leu Ala Glu His
 1               5                  10                  15

Leu Ala Glu Ala Leu Ala Glu Ala Leu Glu Ala Leu Ala Ala
                20                  25                  30
```

PARTICLES

This application is a national stage application of PCT GB98/03071, filed Oct. 14, 1998, which claims benefit of foreign application UK 9721901.8, filed Oct. 16, 1997.

The present invention relates to the targeting of biological cells e.g. for the purpose of analysing for the presence and/or amount thereof in a particular sample or for the purposes of drug delivery.

Biological cells is a term widely used to describe living cells as the entities which substantially comprise the body of a wide range of living organisms, such as micro-organisms (e.g. bacteria, protozoa, fungi, algae), plants and animals. Biological cells may be provided as single cells, as individual cells in a suspension or as cells that may be associated in the form of multicellular organisms or the tissues and organs therein.

It is desirable to be able to monitor for, and/or identify, specific types of cells in a sample. Such cells may be within inanimate material (for instance pathogenic organisms contaminating a food stuff or water supply) or may be mixed with other types of cells (for instance a microbiological infection of a multicellular organism or a cancer cell within a patient).

The metabolic activity of a cell causes changes in the extracellular environment and conventionally such changes have been directly measured by placing a measuring device in, or close to, a medium containing the cells of interest. Thus, for examples, the metabolic activity of cells has been measured by monitoring change in pH, typically resulting from the release of carboxylic acids (such as lactic, acetic acids), changes in gases (such as carbon dioxide and ammonia and their dissolution to form ionic electrolytes) or other protonatable groups (such as amines and amino acids). Typically pH is measured by immersing a pH electrode in the medium continuous with the biological cells. Similar physiological activities have been measured by immersing a conductivity electrode in the said medium, in so far as such measurement results from the changes in the concentration and charge of ionic electrolytes in the said medium. Alternatively, the metabolic activity of cells has been measured with a redox electrode, such as a platinum electrode, which measures the ability of the medium continuous with the cells to donate electrons to, or accept electrons from, an electronic circuit of which the electrode forms one part. Thus, the cells in contact with a medium are the variable part of an electrochemical cell also contacted by at least 2 electrodes, which may measure pH, conductivity or redox potential (in a potentiometric circuit) or Faradaic current (in an amperometric circuit).

The metabolic activity of a cell may also be measured indirectly. For example, a dye may be introduced into the medium containing cells such that the optical properties of the dye (e.g. absorption or fluorescence at a particular wavelength of light) change in proportion to changes in the medium (such as pH or redox potential). Such optical and some electrochemical measurements are also coupled to the activities of enzymes produced by cells. For instance, the activity of hydrolytic enzymes, such as proteases, may be measured by their action on chromogenic or fluorogenic substrates.

There are various inadequacies associated with these conventional measurement techniques. For instance, the magnitude of change in the medium (i.e. the metabolic activity being monitored) wrought by low numbers of cells (typically where cell concentration is less than $10^4$ to $10^5$ cells per ml) is often insufficient to produce a measurable effect. Furthermore similar changes in the medium may be mediated by other cells (which are not of interest) or by materials also present in the medium resulting in multiple or interfering contributions to the measured change, and poor specificity towards the desired measurement. These drawbacks of sensitivity and specificity are especially commonplace in non-specialised devices and assays which are used outside of a specialist laboratory to perform routine measurements.

The detection of micro-organisms such as bacteria in food and/or environmental samples typically requires the presence of at least $10^4$ organisms for measurement over a period of 1 to 4 hours. Theoretically at least, 1 organism or cell can be measured if that cell grows and divides exponentially to a minimum threshold concentration of organisms required by the detection means, however this may take many hours.

Apart from the purposes of analysis, there are other procedures where recognition of cells (e.g. by targeting) are important. One such example is the case of drug delivery. Targeted delivery of a drug to a specific cell type is highly desirable as it removes the need for systemic administration and thereby reduces the risk of non-specific effects or undesirable side effects in non target cells.

Specific agents may be targeted to a cell for the purposes of drug delivery or analysis in a number of ways. For instance, antibodies recognising cell specific antigens may be used to a target a cell. Such antibodies may be directly or indirectly linked to other agents such as detectable labels or a therapeutic agent. Recently particles such as liposomes have been provided with antibodies to form immunoliposomes. These immunoliposomes are useful for targeting any substance contained within the liposome to a cell.

Once a species has been targeted to a cell there is usually a need to induce it to undergo a reaction, or be released, in order that it may exert its desired effect. For instance, when a cell is targeted for the purposes of monitoring for the presence of that cell in a sample, the species may be a detectable label (which needs to be released and/or activated in the vicinity of the cell). In the case of a drug delivery system, the drug may need to be released and/or activated at the target site. One problem associated with known targeting particles, for instance immunoliposomes, is that they have limited utility. This is because release or activation of their contents often depends upon cell mediated endocytosis and subsequent rupture of the liposome inside the cell. However substances targeted to a cell may need to be released extracellularly (e.g. ligands of cell surface receptors) in order that they may exert a desired effect.

It is therefore an aim of the present invention, to obviate or mitigate the disadvantages associated with prior art particles.

According to a first aspect of the present invention, there is provided a lipid vesicle particle capable of being targeted to a cell type of interest, said particle incorporating a peptide which is responsive to a predetermined metabolic signal from the targeted cell so as to modulate the permeability of the particle, said particle further incorporating a species to be targeted to the cell which is activated on said modulation of permeability.

Activation of the species may take a number of forms such as release from the particle and/or conversion (chemical or otherwise). Conversion may occur within the particle or without. Activation of the species also relates to the activation of a chemical reaction by enabling reactants and catalysts (e.g. an enzyme) to interact.

We have found that particles according to the first aspect of the invention are very useful for targeting a species to a cell and then activating that species in the vicinity of the cell. This reaction may be highly sensitive and/or highly selective depending upon the nature of the metabolic signal from the targeted cell.

It is a common characteristic of biological cells that they contain agents, such as enzymes, that perform reactions and other processes, such as the transport of electrons, protons, ions, chemical and biochemical species. Such reactions and, processes are often termed metabolism. Metabolism within a cell often results in a change in the environment surrounding the cell, which environment may also affect the metabolism within the cell. These phenomena will be understood as key aspects of the physiology of the biological cell and are termed herein as metabolic signals.

Suitable particles include any size of particle not too large to mix with and disperse readily in samples containing cells. Particles should be small enough such that they will not sediment in aqueous suspension. Particles may be from a few tens of microns in diameter down to sub-micron sized particles.

The lipid vesicle particles may have an internal aqueous cavity which is isolated from the external environment by at least one layer of enveloping lipids (e.g. phospholipids). The species may be retained within this internal cavity.

The lipid vesicle particles are preferably liposomes and may be multilamella or more preferably unilamella.

The particle may be adapted such that the species is activated in a number of ways. For instance, the permeability of the lipid bilayer of a liposome may be regulated such that permeability across the bilayer may be increased in response to a predetermined metabolic signal. According to the first aspect of the invention this may be achieved by incorporating peptides that act as cytolytic agents into the vesicle. Said peptides may be large proteins or short peptides provided that they are capable of modulating permeability of the particle. These agents may act as or mediate the opening of pores or channels within the lipid bilayer to allow molecules to enter into the vesicle and thereby cause the chemical alteration of the substance contained therein. Alternatively, or additionally, the opening of pores or channels within the lipid bilayer may allow the release of the substance into the extravesicular environment. The cytolytic agents may even cause the rupture of the lipid vesicle to allow the release of the species contained therein. The cytolytic agents are responsive to a chemical or biochemical released from the cell.

The peptide may be an ion channel which "opens" in response to ions (e.g. $H^+$, $Na^+$, $Cl^-$, $HCO^-$, $K^+$ etc.). Alternatively the ion channel may respond to the binding of larger molecules derived from the targeted cell (for instance a growth factor, component of the extracellular matrix of mammalian cells or capsule polysaccharides of micro-organisms). It is also possible to genetically engineer a peptide such that it will be responsive to any predetermined metabolic signal from a selected cell.

The peptide is preferably an integral protein of the lipid bilayer (i.e. the peptide spans the lipid bilayer). However it will be appreciated that the peptide may interact with the bilayer in other ways (e.g. non covalently attached to the outer lipid layer).

Preferred peptides for making particles responsive to a metabolic signal are listed in Table 1.

TABLE 1

| |
|---|
| Aerolysin |
| Amphotericin B |
| *Aspergillus* haemolysin |
| Alamethicin |
| A-23187 (Calcium ionophore) |
| Apolipoproteins |
| ATP Translocase |
| Cereolysin |
| Colicins |
| Direct lytic factors from animal venoms |
| Diptheria toxin |
| Filipin |
| GALA |
| Gramicidin |
| Helical erythrocyte lysing peptide (HELP) |
| Hemolysins |
| Ionomycin |
| KALA |
| LAGA |
| Listeriolysin |
| Melittin |
| Metridiolysin |
| Nigericin |
| Nystatin |
| P25 |
| Phospholipases |
| Polyene Antibiotics |
| Polymixin B |
| Saponin |
| *Staphytlococcus aureus* toxins (α, β, χ, δ) |
| Streptolysin O |
| Streptolysin S |
| Synexin |
| Surfactin |
| Tubulin |
| Valinomycin |
| Vibriolsin |

Preferred particles may comprise 1 mg of peptide for every 1-1,000 mgs of lipid, preferably 1 mg of peptide for every 10-100 mgs of lipid and most preferably 1 mg of peptide for every 30-60 mgs of lipid. However it will be appreciated that the exact ratio of peptide to lipid will depend upon the specific characteristics required in the lipid vesicle particle being formed.

A preferred peptide cytolytic agent is N, Myristic-GALA.

N, Myristic-GALA has an amino acid sequence of W-E-A-A-L-A-E-A-L-A-E-A-L-A-E-H-L-A-E-A-L-A-E-A-L-E-A-L-A-A (where W is Tryptophan, E is Glutamic Acid, A is Alanine, L is Leucine and H is Histidine (SEQ ID NO:1)). The Myristic acid is reacted with the N-terminal (Tryptopan; W) to give N-Myristic GALA.

It will be appreciated that other cytolytic peptides may be used (and particularly those listed in Table 1). For instance particles containing HELP, KALA and LAGA are useful.

Particles according to the first aspect of the invention may be targeted to the cells using selective or specific binding agents. The targeted cells often exist within a population of other non-target cells and it is therefore preferred that the means of targeting the particle has at least some specificity towards the target cell over that of the non-target cells.

The binding of the particle to a target cell (referred to herein as primary binding) may be direct or indirect. Antibodies attached to the particle may be usefully employed for directly binding the particle to antigens on the targeted cell. Thus preferred particles may comprise a liposome with a peptide cytolytic agent and an antibody associated with the lipid bilayer.

It is possible to indirectly bind the particle to a cell by having a binding agent that is not directly connected to the particle. For instance an antibody conjugate could be used which has a moiety which will bind to a particle whereas the antibody portion is capable of binding to the target cell. In this respect biotin may be incorporated in the particle for the purposes of targeting a cell. An antibody conjugated with biotin may be used to bind to a target cell. The "antibody labelled" target cell may then be exposed to avidin which will bind to the biotin on the antibody conjugate. Particles incorporating biotin may then be added to the cells and will specifically bind to the avidin and will thereby be specifically targeted to the cell which has recognised the antibody. A preferred binding protocol using antibodies, avidin and biotin-protein G is described in Example 1. In this case an antibody is bound to a specific antigen in a target cell. After which biotin-Protein G is added (the Protein G binds the antibody) and subsequently avidin is bound to the biotin-Protein G. Finally particles bearing biotin are then bound to the avidin on the complex and are thereby specifically targeted to the cell. It will therefore be appreciated that biotin (or molecules with similar binding properties) may be used in the targeting of cells as well as in the secondary binding process (discussed in more detail below).

A variety of other binding agents are known to those skilled in the art and may be used within the scope of this invention. Peptides may be inserted into the lipid bilayer of a vesicle particle which bind to predetermined structures on the target cell. For instance the fibronectin receptor or an integrin may be used to bind to the extracellular matrix of a cell.

It will be appreciated that it will be possible for a single molecule to fulfil the role of binding agent, to be responsive to the metabolic signal and mediate the adaptation of the particle to allow the release, or activation, of the species contained therein.

Thus it is possible to ensure that a particle according to the first aspect of the invention is targeted with high selectivity and/or specificity (e.g. using an antibody) and also that the particle is adapted (e.g. by incorporating a cytolytic peptide) such that the incorporated species is activated in response to a predetermined metabolic signal.

The species incorporated within the particle may be any chosen compound. For example the species may be a relatively small molecule such as a dye, electrochemical mediator or receptor agonist. The species may also be a fluorescent molecule (such as latex or polystyrene), an antibody, hormone or an enzyme.

It will be appreciated that the species need not be responsive to the metabolic signal from the cell. While it is within the scope of this invention to incorporate species that may be independently responsive to the metabolic signal, it is an important feature of this invention that a wide range of species that are not responsive per se to the predetermined metabolic signal may be used.

Particles according to the first aspect of the present invention may be adapted such that the particle is responsive to a metabolic signal by means of peptides that are easily accessible to a metabolic signal from the outside environment. Ideally the species is held within the particle where it cannot be activated until the peptide on the particle responds to the metabolic signal. Lipid vesicle particles according to the first aspect of the invention represent a technical advance over conventional particles containing responsive species. This is because a species secured inside a conventional particle is in comparatively poor communication with the outside environment and therefore is relatively insensitive to a metabolic signal. Alternatively the species may be on the surface of a conventional particle or retained within a comparatively permeable particle. However this allows the species to be responsive to a target but also often results in non-specific activation of the particle. Particles according to the present invention have the advantage that a species may be sensitively and specifically activated in response to a metabolic signal from a target cell.

Particles according to the first aspect of the invention may be further modified such that the particles are capable of aggregating (referred to herein in as secondary binding). A first particle may be modified such that a first binding moiety is introduced onto the first particle which will bind to a second particle which has a second binding moiety that is capable of interacting with the first moiety. Aggregates may be formed which contain many thousands of particles. The aggregate may form a gel like structure around a cell which may even be large enough to be visible to the naked eye.

Various binding molecules may be used as the first or second moieties to effect secondary binding. Preferred molecules for the first and second moieties are biotin and avidin respectively or biotin and streptavidin respectively. Derivatives and analogues of such moieties may be used. For instance, a Protein A-avidin conjugates or Protein G-avidin conjugates are useful as antibodies may be bound to the conjugates. Such conjugates with antibodies attached, may be prepared in advance of contact with the target cells.

Particles capable of aggregation represent an important feature of the invention because the aggregated particles may be employed in applications which require high sensitivity. Thus according to a second aspect of the present invention there is provided a method of aggregating a plurality of lipid vesicle particles according to the first aspect of the invention comprising providing a first binding moiety on at least some of the particles and at least a second binding moiety on at least some of the remaining particles wherein the first binding moieties interact with the at least second binding moieties such that an aggregate of lipid vesicle particles is formed.

According to a third aspect of the present invention there is provided an aggregate comprising a plurality of lipid vesicle particles according to the first aspect of the invention wherein a portion of said particles have a first binding moiety and a further portion have a second binding moiety capable of binding with said first binding moiety whereby said particles are aggregated together.

The method of the second aspect of the present invention allows large numbers of particles to be brought into close proximity with a target cell. Use of an aggregate of particles allows a species to be accumulated proximal to a target cell in quantities greater than is normally possible when relying on primary binding between the particles and cells.

The secondary binding need not be specific to the target cells, although it is of clear benefit if the aggregation engendered by use of the secondary binding moieties is itself specific and of high avidity. This benefit arises because, unlike known antibody-targeted particles (e.g. fluorescent particles), the particles of the present invention only respond to a metabolic signal (e.g. pH, redox) from the target cell. Thus any aggregates that may form between the said particles which are not associated with a target cell (by primary binding) will not chemically alter and/or release the incorporated species because the necessary metabolic signal is absent. It will be appreciated that it is possible to arrange the aggregation process such as to minimise the number of aggregates not containing the target cell. One way of achieving this is to treat the cells with the particles under such conditions that allow primary binding but few or no aggregates form and then, once primary binding has occurred, a reagent may be added to initiate secondary binding and thereby the formation of aggregates.

When particles modified with avidin and biotin are used secondary binding occurs between the biotin and avidin. The process of aggregating avidin and biotin modified particles may continue until numerous particles form an aggregate of particles around the targeted cell.

It will be appreciated that the specificity of targeting may be improved by ensuring that the secondary binding is also highly specific. To this end secondary binding may be between antibodies (on a first particle) and antigen (on a second particle).

Figure 1:
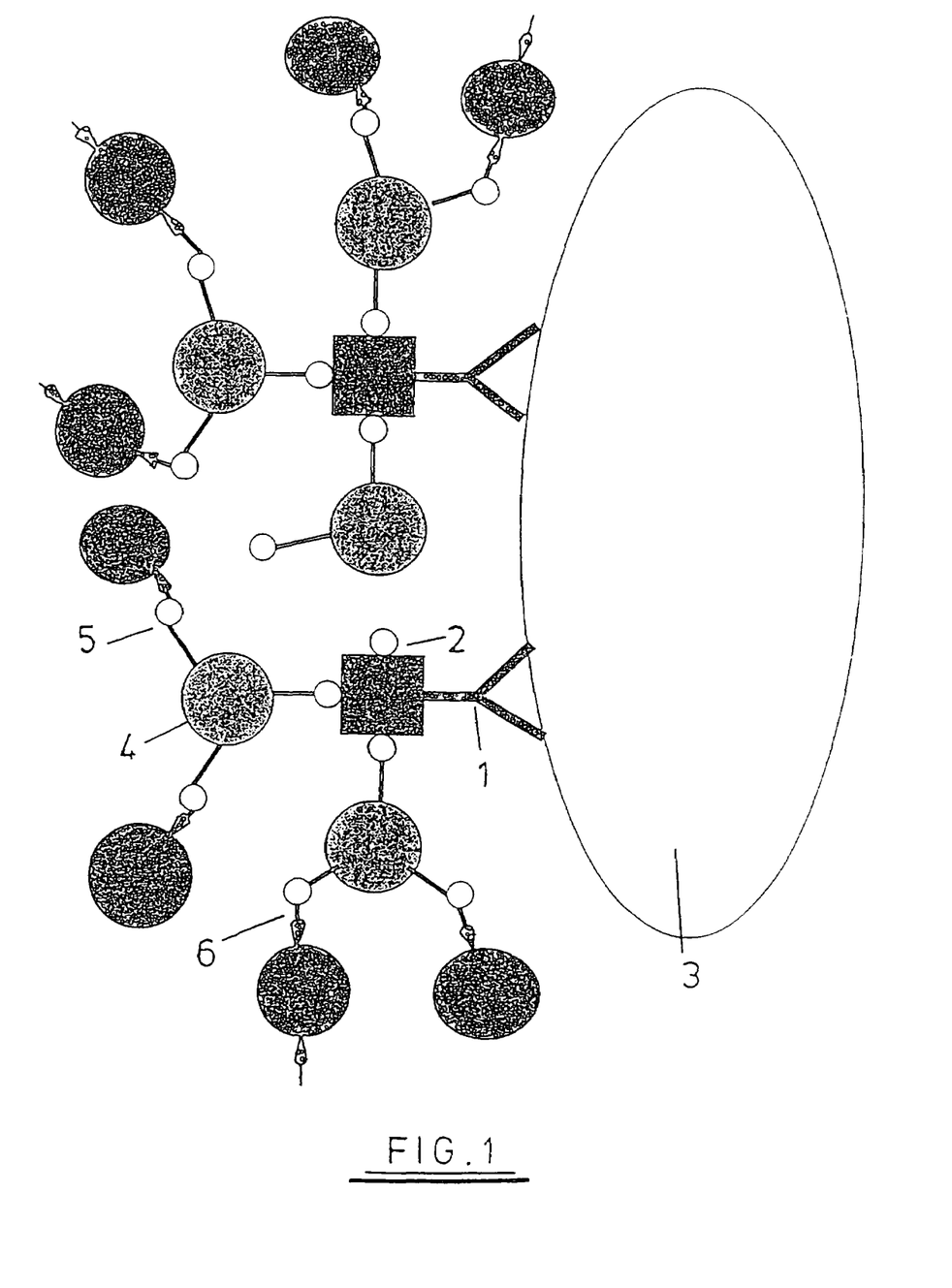
FIG. 1 is a schematic representation of an aggregate of particles according to the invention.

When particles further comprise a binding moiety it will be appreciated that the binding agent which mediates primary binding with the target cell need not be directly attached to the particle. For instance an antibody specific to the cell may be conjugated with a binding moiety which will interact with a complementary moiety on the particle. This antibody conjugate then undergoes a primary binding event with the cell and the particles with moieties complementary for binding with the moiety on the antibody conjugate then initiate the aggregation process. FIG. 1 illustrates a preferred aggregation complex in which the primary binding agent is not directly attached to the particle.

Additional benefits arise from utilising two or more types of particles according to the invention. For instance, two or more populations of responsive particles, which may each incorporate a different species to that incorporated in the other populations, may be used to target a cell or form an aggregate around a cell. By this means, the activation of the species in the different populations of particles (by the metabolic signal) may allow an interaction between the different species such that a desired reaction occurs. This reaction may be the activation of a prodrug into its active form or may be the formation of a detectable compound (when particles are being used for detection purposes). It will be understood that the probability of the first and second populations coming into close proximity is low except where they both bind to the same target cell. Particularly where specific and avid binding takes place, the probability of such a reaction occurring elsewhere in the medium or sample is correspondingly low, particularly where each population must first be activated in response to the predetermined metabolic signal. Thus, when two populations of particle are used, the specificity of activation of the particles will be high.

Particles according to the first aspect of the invention may be used for monitoring for the presence of a cell in a sample or may be used in the diagnostics field for identifying particular cells in the body. This kind of use of the particles represents an important feature of the invention. Thus according to a fourth aspect of the invention there is provided a method of detecting cells which are present or potentially present in a sample comprising treating the sample with a particle capable of being targeted to a cell type of interest, said particle incorporating a species that is directly or indirectly detectable when activated in response to a predetermined metabolic signal from the targeted cell, and monitoring for directly or indirectly the species.

It will be appreciated that the sample may be anything which needs to be tested for the presence of specific cells. The sample may be inanimate (e.g. a liquid sample such as an effluent or water or a solid sample such as a food stuff). The sample may also be ex vivo tissue or even organism (e.g. detection of a specific cell type in a mammal).

The particles used according to the fourth aspect of the invention are preferably particles according to the first aspect of the invention or aggregates of particles according to the second or third aspects of the invention.

However it will be appreciated that other particles may be utilised according to the fourth aspect of the invention. For instance, a particle may be prepared from polymers and comprise structures which change in response to the metabolic signal or alternatively the particle may comprise a microsome formed from surfactants or similar molecules.

As well as containing proteins or peptides which are responsive to a metabolic signal, the particles may be adapted such that the permeability of the lipid bilayer may be regulated by incorporating special cytolytic lipids in the particle. For instance, lipids may be incorporated into the vesicle such that their charge and structure may be altered (e.g. by proton or electron transfer reactions) in response to the metabolic signal. Examples of such lipids include dioleoylphosphatidyl (DOPE)/oleic acid; 1,2 dioleoyl-3-succinyl-glycerol and 1,2 diacyl-3-succinyl-glycerol. This alteration in charge and structure may result in a change in permeability of the lipid bilayer. This permeability change may alter the intravesicular chemical environment and thereby allow the chemical alteration and/or release of substances contained within the vesicle.

The method according to the fourth aspect of the invention may be used to detect cells in a sample or subject with great sensitivity and/or specificity. We have found that the method of the fourth aspect of the invention may be used to directly or indirectly detect less than $10^4$ cells in a sample and as few as $10^1$ cells in a sample within a few hours.

Sensitivity may be further improved by using aggregated particles according to the second or third aspects of the invention.

The method according to the fourth aspect of the invention is particularly useful for the detection of pathogens. Such pathogens may, for example, be in foodstuffs, water samples or even infecting higher organisms. For instance, good food hygiene requires that there is less that 1 pathogenic bacterium (e.g. *salmonella* or *E. coli*) in 25 grams of food or within 1 liter of liquid. Conventional monitoring means, which usually require at least $10^4$ bacteria, are unable to detect such low levels of contamination. Therefore samples of the food or liquid must be cultured to induce the growth of the bacteria (often with a pre-enrichment growth phase followed by selective growth) in order that there are sufficient numbers to detect. This process may take up to 4 days. The method of the fourth aspect of the invention has the advantage that bacterium may be detected within a much shorter time period, typically within a day and frequently within hours. Such time saving is highly significant for hygiene purposes and for the producer who is able to test and then distribute tested foods more quickly.

Particles used according to the fourth aspect of the invention may release a species directly into the medium surrounding the cell from where it may be detectable (for instance a dye may be released from a liposome in response to a metabolic signal from the targeted cell). Alternatively the species incorporated into the particle may be an enzyme. Such an enzyme may catalyse the formation of a detectable product (the substrate may also be incorporated in the particle, may be in the medium or may even be released from the target cell) in response to the metabolic signal from the cell.

Particles used for the detection of cells need not be in direct contact with the medium containing the cells. When this is the case, the medium containing the cells may be in communication with a second medium that contains the particles which respond to changes in the medium containing the cells. These changes may be communicated to the second medium by way of a gaseous phase or through a barrier permeable to the activating species (e.g. pH). For example, microbial activity can be detected by capturing in a second medium carbon dioxide produced by metabolic activity of cells in a first medium. The capture of the carbon dioxide in the second medium typically results in a change of conductivity which may be measured. This conductivity change may be amplified in the second medium by incorporating amplifying species in a particle which responds to the pH change in the second medium to release reagents or enzymes (e.g. asparginase) producing a larger conductimetric response. Similarly, the particles may be retained at high concentrations behind a membrane permeable to proton or redox mediating compounds.

According to the fourth aspect of the invention particles may be directly applied to the sample (e.g. water source, food stuff or even another organism) and the activation of the species within the sample may be detected using a detecting device suitable for the species used in the particle. A preferred way of performing the method of the invention is to place the particles and sample (putatively containing target cells) in or on a gel-like substrate. For instance, the agar plate assay as described in the Examples is a suitable way of performing the method of the fourth aspect of the invention.

A preferred particle for use according to the method of the fourth aspect of the invention incorporates a species that is an amplifier of the metabolic signal from the target cell and thereby increases the sensitivity of the method. Such amplifiers make it possible to detect cells in a sample or within a subject undergoing diagnosis with great sensitivity. The particles may be specifically targeted to the cell of interest following which the substance is chemically altered or released such that the metabolic signal which "labels" the cell is amplified for detection.

Typically, the amplifier is retained within the particle such that the amplifier is not detectable prior to the particle responding to the metabolic signal. When the particle has responded, the amplifier may be released in a measurable form or may react with other reagents in the medium to produce an indirectly measured analogue of the metabolic signal. In this regard, an important feature of the fourth aspect of the invention is that the amplifier per se need not respond directly to the desired metabolic signal and typically does not. Instead, the amplifier is incorporated into a particle whose properties change in direct response to the desired metabolic signal from the targeted cell, the amplifier is released or activated into a measurable form or is allowed to react with other reagents in the medium to form a detectable product.

The amplifier may be a concentrated detectable marker (such as a dye) held inside the particle. Alternatively, the amplifier may be an enzyme or other catalyst. The detectable output from the amplifier in response to the metabolic signal is preferably substantially larger than the signal activating the particle. Thus activation of a particle, such as a sub-micron sized particle containing a dye, by a few tens to a few hundred equivalents may result in the production of at least a few thousand equivalents. In the case of a large molecule (such as an enzyme) correspondingly fewer molecules may be incorporated in the particle compared to a lower molecular weight amplifier. An enzyme-catalysed reaction can turnover many times to produce an equivalent or larger effect. Amplifiers for use according to the fourth aspect of the invention may be selected from a wide range of chemical and biochemical systems, such as inorganics, redox, fluorescent, colourimetrics, luminescent or bioluminescent reagents, enzymes or combination thereof.

When enzymes are encapsulated in particles the enzymes should preferably fulfil at least one of the following criteria:
1. should not be found in the targeted cell;
2. be active under the same conditions over which the peptide is responsive to the metabolic signal (for instance when the peptide is M-GALA the enzyme should be active over the pH range for which M-GALA modulates the permeability of the particle);
3. should have a high specific activity; and
4. be stable when incorporated within the particle.

The detected compound may be formed from more than one precursor. When this is the case, it may only be necessary to incorporate one of the precursors involved in the amplifying reaction in the particle. The other precursors may be found in the medium such that they are isolated from the precursor incorporated within the particle until such a time as the particle responds to the metabolic signal. For instance, when the particle is a vesicle according to the first aspect of the invention, the metabolic signal may increase the permeability of the lipid bilayer and thereby allow the precursors to interact to form the detectable compound.

Purely by way of example, microbial activity can be indirectly detected by measuring carbon dioxide produced by metabolic activity of the cells and/or by measuring pH change in the microbes vicinity (i.e. the carbon dioxide and pH changes are the predetermined metabolic signals to which the particles respond). An increase in carbon dioxide formation results in a change of conductivity which may be measured. This conductivity change may be amplified by using amplifiers incorporated within a particle which are responsive to the pH change (the metabolic signal). The activated particles may release an enzyme (e.g. asparginase) which catalyse a reaction to produce a larger conductimetric response.

By way of further example, microbial activity may be detected using Glucose oxidase encapsulated within a particle. Upon activation the permeability of the particle is increased to allow Glucose oxidase to come into contact with glucose from the outside media. The product of Glucose oxidase activity ($H_2O_2$) may then be acted upon by a further enzyme provided in the media (e.g. Horse Radish Peroxidase) to form a product which is easily detectable colorimetrically (see Example 1 for more details). This may be by use of an instrument or even observed by the naked eye.

Examples of amplifiers which may be incorporated into particles for use according to the method of the third aspect of the invention are shown in Table 2.

TABLE 2

EXAMPLES OF AMPLIFIERS WHICH MAY BE ENCAPSULATED

| Encapsulated Amplifier | Example | Detection Mode |
| --- | --- | --- |
| Enzyme | Alkaline Phosphatase. β-Galactosidase Glucose Oxidase | Enzyme activity coupled to visual, colourimetric, fluorimetric, luminescent, electrosensing measurement |
| Co-Factor or Substrate | Coenzyme A, NAD, NADH FAD, ATP | as Above |
| Fluorphore (self quenching or in combination with quencher) | Calcein, Carboxyfluoroscein | Visual, Fluorimetry, Flow cytometry |
| Chromophore (self quenching) | Arsenazo III | Visual, Absorbance |
| Spin Labels | Tempocholine Chloride | ESR, EPR |
| Ions | Potassium, Calcium | Ion-selective electrodes, Dyes |

An important feature of the method of the fourth aspect of the invention is that the particles may be brought into close proximity with the cells such that metabolic activity occurring in the locality of the cell is more directly responsible for the activation of the species. The close proximity of the particle with the cell means that the metabolic signal is not diluted into the medium bulk, thereby increasing the sensitivity of the overall measurement. The activated detectable species is also more directly coupled to the metabolic activity of the cell, thereby increasing the selectivity and specificity of the overall measurement, towards the cell rather than any similar interfering changes occurring in the bulk medium.

It is not usually practical to increase the proximity between conventional measurement devices and the metabolic changes wrought by cells to minimise the interference and dilution effects apparent in typical media, and particularly those samples containing comparatively small quantities of target cells. In particular, typical samples, such as food and clinical samples, often contain a variety of other non-target cells. Present measurement devices are considerably larger (typically mm to cm dimensions) compared to the cells (typically 0.1 to 50 microns). Thus, particularly in the case where only a few target cells are present in the sample (even when these cells are brought into contact with the measuring device) the measuring device is exposed to large quantities of the sample. Even in the case where the target cells are separated and retained at the measuring device and the bulk of the sample constituents are eliminated, sensitivity at least is not substantially improved for the same reasons.

It is preferred that the method of the fourth aspect of the invention further involves a step by which the particles and targeted cells may be concentrated in a sample. A range of separation methods have been developed to extract and concentrate cells from samples. Many of these methods may be easily modified such that they may be used as techniques for bringing target cells and particles into close proximity, For instance, filtration through membranes designed to retain target cells is widely used for processing water samples containing dilute suspensions and for handling samples of cells in the laboratory. Specific binding proteins, such as antibodies, have also been incorporated onto such membrane filters to retain cells. In both cases, it is possible to co-separate efficiently particles in close proximity to the retained target cells by means of their similar size and their specific binding. Similarly, where such membrane filter or specific binding means are used in conjunction with present measuring devices, it is possible to capture the target biological cells and the responsive particle in close contact with the measuring device to improve the specificity and sensitivity of measurement.

Similarly, a number of phase partition systems, such as dextran and polyethylene glycol solutions, are used to separate cells. Similarities between target cells and the particles (particularly vesicle particles) render their co-separation relatively straightforward. Again, modification of the phase partition media with agents to improve the selectivity or specificity (e.g. using antibodies) of separation of cells can also be applied straightforwardly to co-separate particles with target cells.

Furthermore magnetic compositions, particularly those modified by specific binding agents such as antibodies (immunomagnetic compositions) are widely used to separate cells from other matter. Magnetic and immunomagnetic compositions may be incorporated into the interior or onto the surfaces of the particles according to the first aspect of the invention to form immunomagnetic particles. Thus cells which have magnetic compositions bound to them and magnetic particles can be co-purified.

Particles can also be easily used with separating techniques such as dielectrophooresis (a means of concentrating cells in an asymmetric electric field). The particles (particularly those comprising a lipid bilayer) possess similar surface and physical properties compared to those of cells and can therefore be co-separated. Similarly, they can be co-transported in a dielectrophoretic travelling wave device. Likewise, cells and particles can be co-captured in an ultrasonic standing wave and can be co-transported in an ultrasonic travelling wave.

Particles can also be used in conjunction with means for isolating cells. Thus the cells may be isolated on solid growth media containing selective growth agents in the media or by selective binding agents (e.g. antibodies). In this case the particles can be incorporated into the solid growth media by introduction of the particles into the liquid media prior to the gelation. The particles may also form a layer (e.g. on the surface of the solid media) or they can be impregnated into the surface of pre-formed solid growth media. Alternatively, the said particles can be co-isolated with the target cells on the surface of solid growth media, either by placement of mixtures of cells and particles or by contacting the solid growth media with similar mixtures. Similarly, mixtures of cells and particles can be exposed to selective media designed to enrich or select growth or metabolism of the target cells. Individual biological cells can be placed into separate growth components by micromanipulation or by suitable dilution (e.g. into arrays of micro-well plates) such that they are placed in proximity to the said particles.

A preferred way of performing the method according to the fourth aspect of the invention is to utilise particles aggregated according to the second or third aspects of the invention. For instance when monitoring for the presence of bacteria in a sample, a single bacterial cell may be detected. This can be achieved by monitoring a change in colour on a culture plate from particles containing enzymes which catalyse a reaction which may be monitored colorimetrically. We have found that a colour change which is visible to the naked eye may be observed from a single bacterium about 1 hour after the bacterium has been targeted and an aggregate formed around said bacterium. Hitherto, it has not been possible to resolve a single cell other than by using sophisticated and expensive instruments, such as microscopes and flow cytometers. These instruments require expert use and cannot be applied directly to samples which contain few target cells in a background of a large excess of other bodies in the sample matrix. Therefore, the method of the fourth aspect of the invention (particularly when utilising particles according to the first aspect of the invention) obviate the need for sophisticated instruments for the detection of small numbers of cells. Furthermore the particles serve to increase the specificity and sensitivity of any detection instruments, which those skilled in the field will also understand to mean that the time of detection may also be decreased dramatically using this invention.

The high sensitivity and specificity of methods according to the fourth aspect of the invention means that it is not always necessary to separate the target cells from their original environment and then expose the separated sample to a suitable measuring device. Detectable compounds produced by the responsive particles in proximity to the target cells may be of suitably large magnitude to be resolved by a measuring device, or in the case when amplifiers are used, by the unaided senses of the human body, such as the eye.

The method of the fourth aspect of the invention may be used for diagnostic imaging. Purely by way of example, liposome particles may be filled with a substance which is a precursor of a contrast agent (e.g. for CAT) which is also a substrate for an enzyme found in body fluids. The liposome may be targeted to a desired cell type by use of a specific antibody attached to the surface of the liposome. Furthermore the liposome may incorporate a protein cytolytic agent which is responsive to the metabolism of the target cell such that a change in the permeability of the lipid bilayer allows exposure of the substance to the enzyme and results in the formation of the contrast agent. Targeting of the contrast agent using responsive liposomes improves the sensitivity and resolution of various diagnostic imaging methods.

Under certain circumstances it is not possible to directly measure a detectable response from particles when normal detection procedures are used, such as non-time resolved measurements of optical output. No matter how large the output is made relative to background, the detectable response may not be able to propagate with adequate magnitude through the sample matrix for accurate measurements (especially when the sample is likely to interfere with measurement). When this is the case, gases and vapours (which are advantageously straightforward to measure) are suitable detectable species that may be incorporated in a particle and liberated in response to a metabolic signal. Some gases and vapours may even be detected at low concentrations by the unaided senses of smell and taste. The vapour phase of a liquid or solid sample equilibrates readily with any vapours or gases in the sample which means that gases or vapour are suitable for use with solid samples as well as liquid samples.

Therefore preferred particles for use according to the fourth aspect of the invention may incorporate a gas or vapour which is capable of being released (or formed) in response to a metabolic signal. It is highly preferred that the particle contains substances which may react to form a gas when the particle responds to the metabolic signal. It is more preferred that the particle contains an enzyme which catalyses the production of a gas from substrate in the media (or substrate also provided with the particle). In the alternative, the particle may contain substrates for an enzyme found in the sample which are converted to a gas when the particle responds to the metabolic signal. Table 3 provides a range of typical chemical and biochemical reactions suitable for the production of gases and vapours following particle activation.

TABLE 3

CHEMICAL AND BIOCHEMICAL REACTIONS SUITABLE FOR THE PRODUCTION OF GAS AND VAPOURS FROM PARTICLES

| REACTION | GAS OR VAPOUR PRODUCED |
|---|---|
| Acetylesterase | Alcohol + Acetate |
| Acid Phosphatase | Alcohol |
| Alcohol Oxidase | Aldehyde |
| Alkaline Phosphatase | Alcohol |
| S-Alkylcysteine Lyase | Ammonia + Methyl Mercaptan |
| Amidase | Monocarboxylate + Ammonia |
| Asparaginase | Ammonia |
| Arylesterase | Phenol + Acetate |
| Asides | Nitrogen |
| Bicarbonate | Carbon Dioxide |
| Biotinidase | Ammonia |
| Carbonic Anhydrase | Carbon Dioxide |
| Carboxylesterase | Alcohol & Carboxylate |
| Catalase | Oxygen |
| Catalysts | Various |
| Cysteine Desulphhydrase | Ammonia + Hydrogen Sulphide |
| Deaminases | Ammonia |
| Diamine Oxidase | Aminoaldeyde + Ammonia |
| Ethanolamine Oxidase | Clycolaldehyde + Ammonia |
| α-Glucosidase | Alcohol |
| Glutaminase | Ammonia |
| Hydrides | Hydrogen |
| Lactate Oxidase | Acetate + Carbon Dioxide |
| Metabisulphite | Sulphur Dioxide |
| Pyruvate Decarboxylase | Aldehyde + Carbon Dioxide |
| Redox | Various |
| Serine Dehydratase | Ammonia |
| Sulphides | Hydrogen Sulphide |
| Urease | Ammonia + Carbon Dioxide |
| β-Ureidopropionase | Ammonia + Carbon Dioxide |
| Ureidosuccinase | Ammonia + Carbon Dioxide |

Gas or vapour liberating particles may be used to detect low levels of pathogenic micro-organisms in food by head space vapour analysis at line. Alternatively, the particles may be left in the food to detect subsequent contamination or growth of micro-organisms by the similar accumulation of the vapour or gas in the head space above the food in the food package. Gases and vapours may also permeate into the packaging material which may be impregnated with sensing chemicals whose optical or other properties may be read automatically during shipment, shelf storage or on purchase. Alternatively, pungent vapour or bright colours may be produced to warn of a potential hazard in the food.

An example of a use of gas or vapour liberating particles is for inhalation or ingestion to detect putative infections in the body (such as the throat/lung or in the gut). This may be used to aid diagnosis of said infection or to investigate the effectiveness of therapy, such as antibiotic treatment. In the latter regard, it is a particular advantage of this invention that it targets the micro-organism and releases vapour in proportion to the relative metabolic signal from the micro-organism. By similar means it is possible to determine the susceptibility of a microbial infection to treatment by a particular antibiotic or other therapy. The ability to determine rapidly the susceptibility of micro-organism to such therapy is of course important prior to or when prescribing treatment, particularly in the light of the increased incidence of multiple drug-resistant strains of micro-organisms. In other infections, such as tuberculosis, it is important to establish the compliance of the patient with such therapy.

Purely by way of example a gas generating particle may be made by co-encapsulating the enzyme Carbonic anhydrase with sodium bicarbonate inside liposomes. This enzyme rapidly converts bicarbonate to carbon dioxide in the presence of acid. As cells (e.g. bacteria) produce acid, the pH inside the liposomes will fall when the particle responds to the metabolic signal and carbonic anhydrase will start to produce carbon dioxide. Other possible methods are the encapsulation of asparaginase and asparagine to produce ammonia or urease and urea to produce ammonia and carbon dioxide.

Whereas metabolically responsive particles (particularly particles according to the first aspect of the invention) may be used in the detection and measurement of cells, the same particles may also be used to treat cells. Thus particles which have been targeted to a cell may respond to a metabolic signal and release bioactive substances for the treatment of the cell. Thus, according to a fifth aspect of the invention there is provided a method of treating cells comprising applying to a cell requiring treatment a particle which incorporates a species which modulates cell activity when activated in response to a predetermined metabolic signal from the cells The particles used according to the fifth aspect of the invention are preferably particles according to the first aspect of the invention or aggregates of particles according to the second or third aspects of the invention.

However it will be appreciated that other particles may be utilised according to the method of the fifth aspect of the invention. For instance the particles contemplated above for use according to the method of the fourth aspect of the invention may be used with the exception that species which modulate cell activity may be used.

Treatment of cells according to the fifth aspect of the present invention makes it possible to selectively deliver substances which modulate cell activity to target cells. Furthermore, as the substance is released in response to a metabolic signal from the targeted cell, it is possible to achieve high concentrations of a substance that modulates cell activity in the vicinity of the targeted cell.

Cells may be treated according to the fifth aspect of the invention such that they may be fortified by that treatment. For instance, to encourage the growth of cultured cells (e.g.

by providing a species with growth factor activity to the targeted cell) and especially genetically engineered cells in the biotechnology industry.

Alternatively the particles may contain species which are cytotoxic substances for destruction of the targeted cell. For instance, the particles can be used in the laboratory to destroy an unwanted cell type when it is desired to select between a mixture of cells (e.g. decontaminating a cultured flask of cells that have become fungally infected). The method of the fifth aspect of the present invention is also useful for the decontamination of a water source by introducing into the water particles incorporating a substance with anti-microbial activity.

The particles may also be used for treating animal or humans. Thus according to a sixth aspect of the present invention there is provide a particle capable of being targeted to a cell that incorporates a therapeutically effective amount of a species which is activated in response to a predetermined metabolic signal from a cell, for use in the treatment of medical conditions.

According to a seventh aspect of the present invention there is provided a method of treating medical conditions comprising administering to a patient in need of such treatment a therapeutically effective amount of a particle capable of being targeted to a cell that incorporates a therapeutically effective amount of a species which is activated in response to a predetermined metabolic signal from a cell.

The particles used according to the sixth or seventh aspects of the invention are preferably particles according to the first aspect of the invention or aggregates of particles according to the second or third aspects of the invention.

However it will be appreciated that other particles may be utilised according to the sixth or seventh aspects of the invention. For instance the particles contemplated above for use according to the method of the fourth aspect of the invention may be used with the exception that species which have therapeutic efficacy may be used.

The therapeutically effect species may be a therapeutic substance which is activated by metabolic signals in the locality of a target cell. Such substances are already known (for instance activation of substances by changes in redox chemistry for cancer therapy). However, according to the sixth or seventh aspects of the invention, the particle per se responds to the metabolic signal. This is advantageous because the use of responsive particles makes it unnecessary for the therapeutic species per se to be responsive. Thus a wide range of therapeutic species may be incorporated into the particle, whereas previously only a limited number of responsive substances (which are expensive to manufacture) were available.

The particles may be used to deliver drugs for the treatment of almost any medical condition. However the particles are highly suitable for the delivery of drugs which need to be carefully targeted. For instance the particles are useful for delivering drugs with narrow therapeutic windows (e.g. some forms of chemotherapy) or for the delivery of drugs with serious side effects on none target tissues. Generally the particles are useful when general systemic administration of a drug is undesirable.

The particles are particularly useful for the destruction of cancer cells and may be used to deliver chemotherapeutic agents or radiotherapeutic agents. Cancer cells often possess at least one distinct surface structure suitable for binding the particles and often have a distinct physiology, such as a higher growth rate, often affecting the poise of physiological conditions, such as redox, in their locality. Therefore cancers are most suitably targeted with the particles.

The particles are also useful for treatment of microbial infections, for example a bacterial infection. For instance, an aerosol of particles containing an antibiotic may be inhaled to combat a respiratory infection. By way of further example we have found that a particle loaded with an antibiotic may be used to target and kill bacteria which infects blood. Thus the particles are useful for treating septicaemia etc.

The particles may also be used according to the sixth or seventh aspects of the invention in the treatment of other conditions. For instance, cells involved in the immune responses of the body may be treated using particles incorporating therapeutic agents. In some conditions, such as autoimmune diseases, it may be beneficial to suppress particular cells involved in the attack of body tissues, in other conditions, such as poor cellular or immune responses against infections or cancers, it may be beneficial to promote the development, growth or metabolism of particular cell populations or sub-population in order to engender improved protection against such conditions.

The particles according to the sixth or seventh aspects of the invention is also a useful means of treating conditions in which cells found in very low numbers may be harmful to the subject (for instance small and/or newly developed malignant tissues).

The use of more than one type of particle allows the targeting of more than one type of drug to the same site of action. Therefore if two components are required to form an active drug, each could be provided in a different particle. Alternatively several drugs may be delivered to the same target site (e.g. several different antibiotics for multi drug resistant infections). It also possible to target many particles to the site of action using a minimal quantity of antibody when different drug bearing particles are aggregated around the target cell. Aggregation of particles also allows targeting of a greater quantity of less potent or less soluble drug to the site of action. All of the systems described above are activated by the metabolic signal from the target cells thus negating any non specific binding or antibodies to other cells.

Embodiments of the present invention will now be described, by way of Examples, with reference to the accompanying drawings.

FIG. 1 illustrates a preferred aggregation complex of particles according to the fifth aspect of the invention. In FIG. 1, antibodies 1 are conjugated to a first binding moiety 2 and make the primary binding interaction with the target cell 3. Particles 4 with a plurality of second binding moieties 5 then aggregate around the conjugate by means of complementary binding between the first 2 and second 5 binding moieties. The aggregate may be enlarged by the addition of further particles with a further binding moieties 6 (which may or may not be the same as binding moiety 2) which then bind to a second binding moiety 5. It will be seen that the size of the potential aggregate will only be limited by the availability of further particles with binding moieties.

EXAMPLE 1

Particle according to the first aspect of the invention were manufactured according to the following protocols. The particles were capable of aggregating according to the method of the second aspect of the invention by the addition of biotin. The particles were then utilised in a method of detecting for the presence of bacteria according to the fourth aspect of the invention (1.4).

1.1. Manufacture of Biotinylated Liposomes Encapsulating Glucose Oxidase

Phosphatidyl choline (Sigma P-3556) 40 mg, Cholesterol (Sigma C8667) 11 mg, Dihexadecyl phosphate (Aldrich 27, 149-7) 2.8 mg were dissolved in 5 ml 1:1 Chloroform:methanol (both BDH HiPer Solv) and added to a 50 ml round bottom flask. 0.272 mg, Biotin-DPPE (Pierce 22008) was made up as 1 mg/ml in 1:1 chloroform:methanol and added to the flask which was then evaporated to dryness on a rotary evaporator. The flask was then placed on a freeze-drier for at least one hour to remove any last traces of solvent.

The resultant lipid film was then hydrated with 13 mg of Glucose Oxidase (GOD) in 7.5 ml Tris buffer pH 7.1 and stored overnight in the fridge, prior to freezing in liquid nitrogen and subsequent thawing in a water bath. This was repeated five times.

The liposomes were then extruded (extruder—Lipex Biomembranes Inc. Vancouver Canada) twice through a 0.4 micron and then ten times through a 0.2 micron polycarbonate membrane using a oxygen free nitrogen of between 5 and 40 bar pressure. Storage of the liposomes was at 22° C. after extrusion and at all steps thereafter. The liposomes were then purified using gel filtration using a Sepharose CL-6B column (Sigma CL-6B-200) and 10 mM Tris(hydroxymethyl) aminomethane (Sigma T1503) buffer 017.1. The column had a total volume of 50 ml CL6B with a void volume of 14 ml, 2 ml aliquots of unpurified liposomes were added to the column and 1 ml fractions collected of the optically turbid eluent. Each fraction was then assayed for unencapsulated and encapsulated enzyme activity as described below 1.2 Assay of Liposomes Encapsulating an Enzyme Species (Glucose Oxidase)

Liposomes were assayed in order that those encapsulting GOD could be selected.

1.2.1 Spectrophotometer Procedure

Two solutions, A and B, were prepared:
A: 300 mg D-glucose and 200 International Units Horseradish Peroxidase (HRP, Sigma P6782) in 20 mls 50 mM Sodium Phosphate buffer pH6.
B: 1 mg/ml 5-Amino-salicylic acid (5-ASA. Sigma A3537) in Phosphate buffer pH 6 (a substrate for HRP).
0.5 ml of A and 0.5 ml B were placed in a cuvette and used to zero a UV/Visible spectrophotometer at 450 nm.

(a) 30 µl of liposomes (1.1) were added to the cuvette. Glucose oxidase activity in the cuvette was then measured to assess the extent of encapsulation. Any resultant enzymic activity was due to unencapsulated GOD which was either free in solution or bound to the exterior of the vesicles. Thus the lower the measured activity the better the encapsulation of GOD.

(b) Next, 10 µl 10% Triton X100(Pierce28314) was added to the cuvette (to cause lysis of the particles). The cuvette was agitated and replaced in the spectrophotometer. The enzyme rate of the lysed liposomes was then measured to assess total GOD in the sample.

Liposome fractions with high encapsulated enzyme and low background signal were pooled, the remainder were discarded.

1.2.2 Further Purification of liposomes Incorporating GOD

Liposomes were further purified by passing liposome fractions down a Concanavalin A-Sepharose 4B column (Sigma C9017) to bind the glucosyl part of the glycoprotein GOD. This further removed GOD bound to the exterior of the liposomes.

Alternatively further purification was achieved by hydrophobic ion chromatography using Aminopropyl glass beads (Sigma G 5019) or Trypsin bound to glass beads (Sigma T 8899). Liposomes were added to the beads (1 ml to 100 mg) and incubated on a roller mixer for 14 hours.

Failure to remove enzyme hound to the exterior of the liposomes results in a high non-specific background signal, making bacterial detection impossible.

1.2.3 Avidin Aggregation.

The presence of biotin on the outside of the liposomes was confirmed by aggregating the liposomes with avidin.

A spectrophotometer was set to 600 nm and 1 ml Tris buffer pH 7.1 used as a blank. 100 µl of purified biotinylated liposomes was added to 1 ml Tris pH7.1 and a relatively flat line was seen versus time indicating the initial turbidity of the liposomes. 30 µl aliquots of 1 mg/ml Avidin were added to this cuvette until the absorbance began to decrease indicating avidin saturation whereby the liposomes no longer aggregate.

Addition of a sufficient amount of avidin caused the liposomes to aggregate thus increasing the turbidity of the sample (measured as an increase in absorption in a spectrophotometer). The addition of further avidin caused the formation of very large aggregates which fell out of suspension (hence decreasing absorbence). Excess avidin results in the formation of small aggregates which lead to reduced detectable signal.

1.3. Incorporation of a Cytolytic Peptide (M-Gala)

A particle according to the first aspect of the invention was formed by incorporation of M-GALA into the lipid bilayer of the liposome formed according to method 1.2.

N, Myristic-GALA has an amino acid sequence of W-E-A-A-L-A-E-A-L-A-E-A-L-A-E-H-L-A-E-A-L-A-E-A-L-E-A-L-A-A (where W is Tryptophan, E is Glutamic Acid, A is Alanine, L is Leucine and H is Histidine (SEQ ID NO:1)). The Myristic acid is reacted with the N-terminal (Tryptopan; W) to give N-Myristic GALA.

M-GALA makes the particle pH sensitive and is therefore responsive to a metabolic signal from a target cell (cells tend to acidify their environment). A decrease in pH causes a conformational change in M-GALA which increases the permeability of the lipid bilayer of the particle and thereby allows the activation of HRP (which proceeds to catalyse oxidation of glucose in the extravesicular environment).

Liposomes (from 1.2) were filter sterilised through a 0.22 um filter. A solution of 0.1 mg/ml M-GALA in demineralised water was prepared by adding a few crystals of ammonium carbonate to dissolve. This was then also filter sterilised. 500 µl sterilised liposomes and 750 µl sterilised M-GALA solution (or proportions thereof) were mixed and incubated at room temperature for 30 mins.

It was found that the quantity of M-GALA used was critical for the successful preparation of particles according to the first aspect of the invention. Too much peptide causes premature release of the species contained within the liposome whereas too little resulted in the particle being unresponsive to the metabolic signal.

1.4 Detection of Bacteria According to the Method of the Fourth Aspect of the Invention Bacteria were detected using the abovedescribed particles. GOD and HRP were exploited in a linked enzyme assay which yielded a colored product indicative of the presence of bacteria. The activation of particles lead to the GOD mediated production of $H_2O_2$. This in turn was reacted with 5-ASA (mediated by HRP) to give an easily detectable complex coloured product. The presence of coloured product indicating that the particles had responded to the metabolic signal and that the targeted cells were present. It will be appreciated that the amount of colour produced may be quantified to give an indication of the number of targeted cells present.

An agar plate assay was performed to illustrate the usefulness of the particles for detecting bacteria in a sample.

1.4.1 Media Preparation

Agar media was prepared comprising Peptone (5 g/Liter). Yeast extract (2 g/Liter), Glucose (10 g/Liter) and Agar (15 g/Liter).

Prior to pouring the plates 1 mg/ml 5-Aminosalicylic acid (20% to final media volume) was filter sterilised and added to the plate with 0.1% (to final volume) sterile HRP (100 IU/ml). When poured and set, the pH of the plates was checked to ensure that it was above 6.8. Alternatively the 5-ASA was added to the media prior to autoclaving as this produced agar plates with a more uniform pH across the surface. If pH 6 plates were required the media was adjusted to pH 7 before autoclaving, for pH 7 plates the media was adjusted to pH 8.3 before autoclaving.

1.4.2 Bacterial Detection.

A *Salmonella* culture was grown in TSB (Oxoid CM 129) or BHI (Oxoid CM225) media overnight at 37° C. In the morning it was sub-cultured into fresh media and allowed to grow for a further 2 hours ensuring that the culture was in the log phase of growth. Serial dilution of the culture was performed in PBS.

1 mg CSA antibody (Bactrace 01-91-99) and 1.3 mg Avidin (Sigma A9390) were dissolved in 833 ul sterile PBS and filter sterilised. Then, 167 ul of 1 mg/ml Protein G-Biotin (Sigma P8045) in PBS was filter sterilised and added. The mixture was incubated together for 30 mins.

20 μl of the CSA antibody Protein G-Biotin Avidin complex was added to 1 ml of bacterial dilution and incubated for 90 mins. This mixture was centrifuged at 13,000 g for 10 mins, and the supernatant discarded. The pellet was resuspended in 1 ml PBS, spun down again and the supernatant discarded (removing unbound complex and excess avidin).

10 μl of particles (see 1.4) and 900 ul of PBS was then added and the mixture incubated for a further 30 mins prior to the addition of 20 μl sterile avidin to aggregate the liposomes. Following a further 60 min incubation the mixture was centrifuged at 0.1 g for 4 minutes and then allowed to stand for 15 minutes to assist settling of the aggregated complex. The supernatant was carefully removed and the pellet was then resuspended in 20 ul PBS and this volume was then added to the dried agar plate. The plate was incubated at 37° C. and observed at half hourly intervals up to 6 hours.

1.4.3 Results

The presence of a coloured product of the HRP mediated reaction was indicative of the presence of bacteria in the sample (a positive result).

Experiments were performed which compared heat and formalin killed cells (as controls) and cells treated as described above. Colour development was tested in two types of *salmonella*.

For live samples of *S. enteritidis* a sample containing 185 cells was positive in 30 mins whereas a sample containing 18 cells was positive in 2 hours. For live samples of *S. typhimurum* a sample containing 115 cells was positive in 1 hour whereas a sample containing 11 cells was positive in 2 hours. Control samples of killed cells gave no signal.

These results demonstrate the speed at which the method according to the fourth aspect of the invention may be used to detect bacteria. Furthermore the method may be used to distinguish viable cells from dead cells.

Detection is possible of approximately $10^1$-$10^2$ colony forming units within 2 hours. This greatly improves time of detection over conventional methods and allows the detection of cells in a sample containing $10^2$ viable cells (or less) in a single working day.

1.5 Detection of Bacteria According to the Method of the Fourth Aspect of the Invention in Foods 1.5.1 Selection of Foods for Testing The method of the fourth aspect of the invention was used (employing the abovedescribed particles) to test for the presence of *Salmonella* in various foods. The British Standard Method for detection of *Salmonella* (BS5763: Part 4:1990) was also performed on the food samples to assess the sensitivity and selectivity of the method of the invention.

The foods tested were whole eggs, dried skim milk powder, milk chocolate, raw minced beef, cooked chicken and raw cabbage. Foods were selected on the basis of the following criteria:

a) Inclusion of food from major food groups (meat/fish, dairy, vegetables)

b) Inclusion of food subject to different processing conditions (raw, cooked, dried)

c) Inclusion of foods with a range of nutritional compositions (fat, protein, carbohydrate content)

d) Inclusion of major food vectors for *Salmonella* e) Inclusion of foods rich in biotin and/or avidin such as eggs and skimmed milk. This category was included to assess the possibility of interference from the avidin/biotin in the food on binding of the biotinylated liposomes to the CSA Antibody/Protein G complex (see above).

Test samples of food were spiked with 10-100 (low) cfu of target organism (*S. enteritidis*), a $10^4$-$10^6$ (high) cfu of target organism (*S. enteritidis*) or left unspiked (control sample S). All foods were analysed in duplicate for each spike level.

The inoculum for spiking was prepared by diluting an overnight BPW culture of *S. enteritidis* in PBS to $10^{-6}$ (for the low level spike) and $10^{-3}$ (for the high level spike). The food samples were then inoculated with 0.1 ml of the $10^{-3}$ dilution (low level spike) or 1 ml of the $10^{-3}$ dilution (high level spike). The number of organisms spiked into the food samples was checked by plating out the PBS dilutions, in duplicate, onto Plate Count Agar using a spread plate technique. The plates were incubated for 24 hours at 37° C. after which colonies were counted.

25 g of each food sample was mixed with 225 ml Buffered Peptone Water broth, and then spiked with *S. enteritidis* as described above and then incubated for 16-20 hours. The broth was then diluted 1 to 10 using PBS prior to testing with the particles.

1.5.2 Results

*Salmonella* was detected in all of the food samples containing bacteria (both high and low spiked samples) using the method of the fourth aspect of the invention. There were no false negative results.

In contrast the BS method gave false negative results for some of the "low" spiked food samples (one replicate each of the mince beef and cabbage low spikes).

Thus the method of the fourth aspect of the invention provided a way in which bacteria can be detected in food samples which represents an improvement over a conventional testing method.

EXAMPLE 2

Particles according to the first aspect of the invention were manufactured which contained Asparaginase as the species incorporated within the liposome. These particles were used in a bacterial detection method according to the fourth aspect of the invention that involved assaying changes in conductivity (the metabolic signal) mediated by the target bacteria.

In the conductivity method, pH changes caused by the *Salmonella* bacteria in a sample result in a pH sensitive cytolytic peptide (M-gala) in the liposome particle mediating the release of asparaginase from the liposome. The released asparaginase reacts with asparagine in the media to cause a further increase in conductivity ($NH_3$ production) and thereby acts to amplify the change in conductivity mediated by the bacteria per se.

Reaction mediated by asparaginase:

L-asparagine+$H_2O$→L-asparate+$NH_3$ 2.1 Manufacture of Liposomes Encapsulating Asparaginase Asparaginase (1000 IU/ml, CAMR, Porton Down) was prepared by diluting the freeze-dried contents of a 10,000 unit vial in 0.22 µm filter sterilised demineralised water to 1,000 units per ml and stored in the freezer in 1 ml aliquots until required.

Phosphatidyl choline (Sigma P3556) was made up as 50 mg/ml in a 1:1 mixture of chloroform:methanol and was stored in the freezer prior to use. 800 µl of this mixture was removed and placed in a 50 ml round bottom flask. 11 mg of cholestrol (Sigma C8667) was weighed out and dissolved in 2 ml chloroform:methanol (1:1 v/v) and also added to the round bottom flask. Next, 2.8 mg of dicetyl phosphate (Sigma D2631) was weighed out and dissolved in chloroform:methanol and also added to the round bottom flask.

The sample was rotary evaporated using a water bath set at 35° C. until all the solvent had been removed leaving behind a thin lipid film on the flask. The flask was then placed on a freeze-drier overnight to ensure that all last traces of solvent were removed.

6 ml of demineralised water was then added, along with 754 µl 100 mM Tris pH7 and 750 µl asparaginase (1,000 IU/ml) to the flask and mixed gently for 2 hours at room temperature. After this time the lipid mixture was immersed in liquid nitrogen until completely frozen. The mixture was then immersed in a water bath set at 35° C. until completely melted. The freeze-thaw process was performed five times in total.

An extruder was assembled with a drain disc followed by two 0.4 um membranes. The lipid mixture was then passed through the extruder twice with the minimum of pressure from the oxygen free nitrogen line. The discs were then changed for two 0.2 um discs and the lipid mixture passed through ten times in total. The resulting liposomes were then stored in a fridge.

The liposomes were purified to remove any excess enzyme that had not been encapsulated. This was performed by adding 100 mg Trypsin attached to DITC glass beads to 1 ml of liposomes and mixing for 11-12 hours at room temperature. The beads were washed in demineralised water prior to use to remove stabilizer. After the incubation period the beads were removed by centrifuging at 13,000 rpm for 10 minutes. The liposomes were removed and stored at refrigeration temperatures.

In order to make the liposomes pH sensitive, the M-GALA peptide was inserted into the lipid membrane. This was achieved by incubating the M-GALA solution (0.1 mg/ml) with the liposomes in equal volumes for 30 minutes.

2.2 Conductivity Tests.

Tests were carried out on a Don Whitley Scientific RABIT (Rapid Automated Bacterial Impedance Technique) instrument. The system uses individually assembled plastic cells with two electrodes in the bottom. The plastic cells sit in a module maintained at 37° C. attached to a computer from which the instrument is run. Media (minimum 2 mls) is placed in each cell and the system set to read the conductivity of each of the 32 cells every minute for up to 24 hours.

Bacteria to be targeted were grown in specifically formulated selective media which has a low conductivity. Growth of the bacteria causes the conductivity of the media to increase and changes in conductivity over time are plotted. When pH sensitive liposomes are introduced to the system the liposomes lyse as the cells grow and lower the pH, and hence the asparaginase/asparagine cause the conductivity of the solution to change faster than the action of the cells alone.

Tests were conducted as follows: 2 mls of media was introduced to a RABIT tube and allowed to stabilise for 30 mins. After this time 200 µl of substrate (30 mM asparginine), 50 µl of peptide (0.00025 mg/ml M-gala) and 100 µl of liposomes 9 see 2.1) were added to the tube along with a dilution of a bacterial culture. The modules were run at 37° C. for between 8 and 24 hours taking readings every 1 minute. Over this time the *Salmonella* grew, produced acid, which cause lysis of the liposomes and hence increased the measured conductivity. This increase in conductivity showed as a growth curve plotted by the RABIT software.

2.2 Results

We have found that the use of particles according to the present invention containing a suitable amplifier (such as asparaginase) results in an accelerated detection time (approximately 2 hours) for the targeted bacteria. This may be compared to the 8-24 hour detection time required for most *Salmonella* species using selective media alone.

2.2.1 Conventional Detection of *Salmonella*

Figure 2:
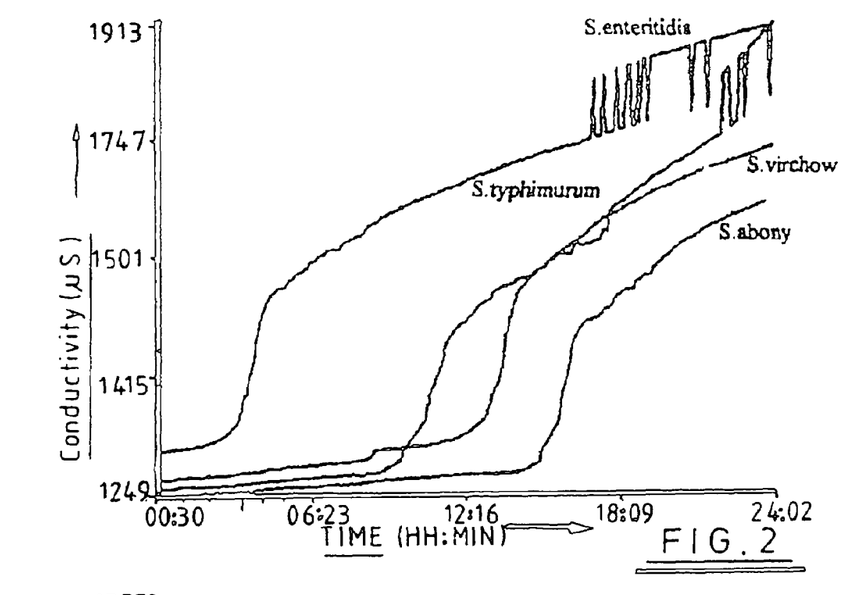
FIG. 2 is a graph of Growth curves of four *Salmonella* species in Example 2.

Time for detection was determined as the time taken for a sigmoidal growth curve to be seen. Four species of *Salmonella* were grown in TMAO at 37° C. for 24 hours in the absence of particles (see FIG. 2). As expected, time for detection varied between species and was between about 6 hours for *S. enteritidis* and 20 hours for *S. abony*.

2.2.2 Liposome Sensitivity Tests.

The times to detection on the RABIT using the method according to the fourth aspect of the invention was carried out using a dilution series of an overnight *Salmonella* culture, as this also gave an indication of the numbers required for the accelerated method to be beneficial, i.e. the sensitivity of the method.

Figure 3:
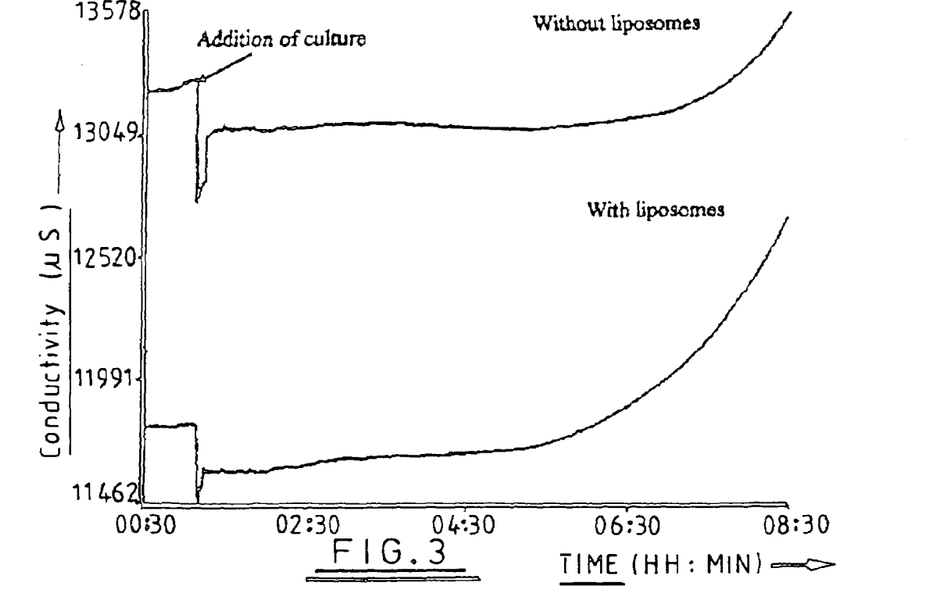
FIG. 3 is a graph of a Growth curve of *S. enteritidis* with and without liposomes with a starting innoculus of $2 \times 10^8$ cfu/ml from Example 2.
Figure 4:
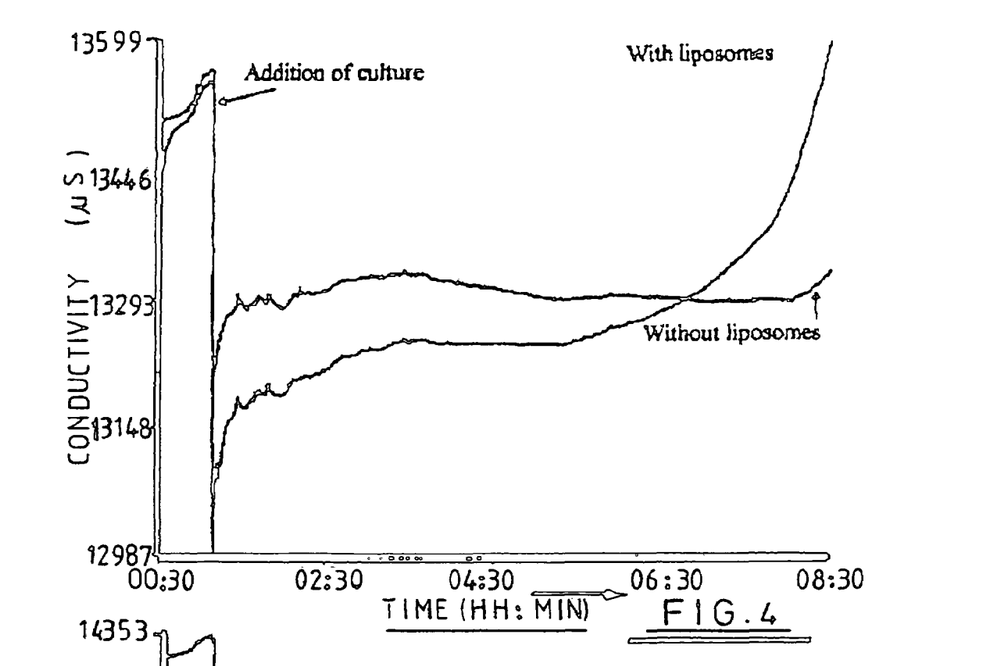
FIG. 4 is a graph of a Growth curve for *S. enteritidis* with and without liposomes with a starting innocula of $2 \times 10^7$ cfu/ml from Example 2.
Figure 5:
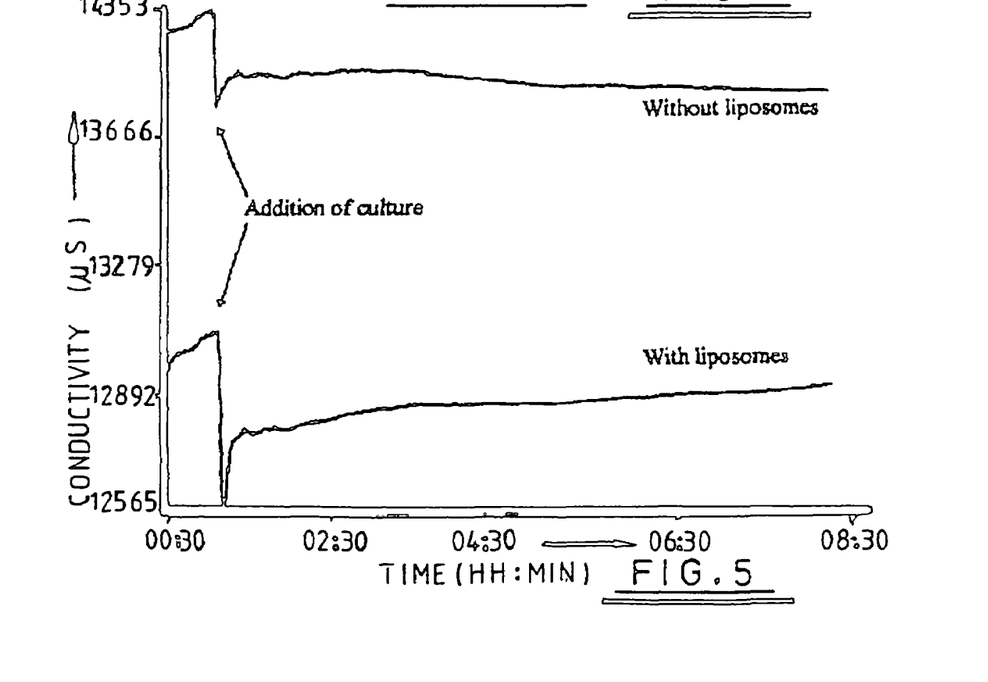
FIG. 5 is a graph of a Growth curve for *S. enteritidis* with and without liposomes with a starting innocula of $2 \times 10^6$ cfu/ml from Example 2.

FIGS. 3, 4 and 5 illustrate the growth of *S. enteritidis* of ($2\times10^8$ cfu/ml, of $2\times10^-$ cfu/ml and of $2\times10^6$ cfu/ml respectively) in the presence of the liposomes constructed according to protocol 2.1.

These data show that for the $10^{-1}$ dilution of *S. enteritidis* (approximately $10^8$ cfu/ml), the logarithmic growth phase was detected after about 5 hours in the presence of particles and 7 hours for a control (i.e. in the absence of particles). The $10^{-2}$ dilution ($10^7$ cfu/ml) also showed an approximate 2 hour acceleration in the presence of particles.

Control experiments confirmed that conductivity in media containing particles (but no bacteria) was at a low level because the particles remained unactivated whereas addition of triton resulted in rapid increase in conductivity as lysis of the particles liberated asparginase into the medium (which contained the aspargine).

EXAMPLE 3

Particle according to the first aspect of the invention were manufactured according to the following protocols. The particles were then utilised according to the fifth and sixth aspects of the invention to eliminate bacteria from a sample of blood.

3.1. Preparation of Particles Containing Gentamicin 50 mg Phosphatidyl choline and 13 mg Cholesterol were dissolved in chloroform/methanol (1:1 v/v) in a round bottomed flask and then evaporated to dryness using a rotary evaporator and a water bath at 50° C. The flask was then placed on a freeze drier overnight to ensure no trace of solvent remained. The lipid film was then hydrated with 2 ml of 10 mM Tris HCl buffer containing 20 mg Gentamicin sulphate (Sigma G 3632) for 2 hours on a flask shaker prior to storage in the fridge overnight. The mixture was then frozen in liquid nitrogen and subsequently thawed in a water bath, this process was repeated tour times in total. The liposomes were then extruded twice through a 400 nm polycarbonate membrane followed by ten passes through a 200 nm membrane. The liposomes were then purified by gel filtration (PD 10) prior to storage at room temperature. Lysed liposomes were added to spread plates growing a lawn of *S. Typhimurium* and much larger zones of inhibition observed compared to unlysed liposomes, demonstrating that gentamicin was encapsulated within the particles (data not shown).

3.2 Preparation of Erythrocytes

Fresh rats blood was obtained with sodium heparin added to prevent clotting. Following centrifugation at 600 g for 10 mins and discarding of the supernatant, the pelleted erythrocytes were resuspended and washed three times in isotonic sucrose-glucose phosphate buffer (0.2M sucrose, 0.1M glucose 10 mM sodium phosphate, pH 7.3). Erythrocytes were used on the same day.

3.3 Haemoglobin Assay

Leakage of haemoglobin from the erythrocytes (50 µl aliquots) was assayed spectrophotometrically at 578 nm against isotonic sucrose glucose phosphate buffer. Percentage lysis of the erythrocytes was established by construction of a standard curve. The supernatant from the centrifuged cells (3.2) represented 0% whereas 100% lysis obtained by incubation with 20 ul 10% v/v Triton X100 for 10 minutes.

3.4 Preparation of Liposome Antibody Conjugates 1 mg CSA antibody was dissolved in 750 µl phosphate buffered saline (PBS) and filter sterilised through a 0.22 um filter. To this was added 250 µl sterile biotinylated protein G and the mixture was incubated for 30 minutes at room temperature. 60 µl of the complex was added to sterile eppendorfs followed by 100 µl of sterile gentamicin liposomes. Two separate aliquots of sterile 30 µl avidin (1 mg/ml) were added to the eppendorfs, 10 minutes apart and the mixture was incubated for 30 minutes to produce a CSA antibody-Protein G-biotin-avidin-aggregated biotin liposome complex. Each eppendorf then had 100 µl of sterile M-gala peptide (0.1 mg/ml) added and this was then incubated for a further 30 minutes.

3.5 Elimination of Bacteria in the Presence of Erythrocytes

*S. Typhimurium* was grown up in tryptone soya broth and then diluted into PBS to 4600 colony forming units per ml (by viable count). 5 µl of diluted bacteria were added to 50 µl erythrocytes in 1 ml sucrose glucose phosphate buffer followed by 100 µl of liposome antibody complex and the mixture was incubated for 30 minutes.

3.2 Results

Cultures were centrifuged at 600 g for 10 minutes and the supernatant examined spectrophotometrically as described above to assess erythrocyte lysis. In the presence of particles (but no bacteria) erythrocyte lysis varied between 0.88 and 0.61% with a mean of 0.73%. Addition of M-GALA alone to erythrocytes produced a lysis of 0.31%. No lysis occurred for erythrocytes left in buffer only.

Bacteria, erythrocytes and liposome complexes were plated on both nutrient agar and Rambach agar plates and the colonies counted after incubation at 37° C. overnight. Of samples grown in the presence of particles only 0.95% of bacterial colonies were observed compared to untreated organisms plated directly from the PBS dilution. In contrast, 76.1% of organisms survived the control experiment performed with erythrocytes. This demonstrates the survival of erythrocytes in a targeted liposome complex which effectively killed *S Typhimurium*.

The invention claimed is:

1. A method of detecting a cell type of interest present or potentially present in a sample comprising treating the sample, in vitro or ex vivo, with lipid vesicle particles which specifically bind to said cell type of interest, said particles having at least one layer of enveloping lipids and incorporating a cytolytic peptide, which is non-covalently attached thereto, wherein said peptide, in response to a predetermined extracellular metabolic signal from said cell type of interest, if present in the sample, interacts with the layer to act as or mediate the opening of pores or channels within the lipid layer to thereby modulate the permeability of the particles, said particles further incorporating a species which is released on said modulation of permeability, wherein said species produces a detectable signal in the presence of said metabolic signal, and monitoring directly or indirectly for the species, wherein a portion of said particles have a first binding moiety and a further portion of said particles have a second binding moiety which is capable of binding with said first binding moiety whereby said particles are, or are capable of being, aggregated together, and wherein said sample is treated with said particles under conditions such that a collection of said particles is aggregated around said cell type of interest.

2. The method according to claim 1, wherein the first binding moiety is avidin or a derivative thereof, and the second binding moiety is biotin or a derivative thereof.

3. The method according to claim 1, wherein said cell type of interest is pathogenic cells.

4. The method according to claim 3, wherein said method is a method for analysing foodstuff for the presence of said pathogenic cells.

5. The method according to claim 3, wherein said method is a method for analysing water samples for the presence of said pathogenic cells.

6. A method of detecting a cell type of interest present or potentially present in a sample comprising treating the sample, in vitro or ex vivo, with lipid vesicle particles which specifically bind to said cell type of interest, said particles having at least one layer of enveloping lipids and incorporating a cytolytic peptide, which is non-covalently attached thereto, wherein said peptide, in response to a predetermined metabolic signal, which metabolic signal comprises a change in pH, from said cell type of interest, if present in the sample, interacts with the layer to act as or mediate the opening of pores or channels within the lipid layer to thereby modulate the permeability of the particles, said particles further incorporating a species which is released on said modulation of permeability, wherein said species produces a detectable signal in the presence of said metabolic signal, and monitoring directly or indirectly for the species, wherein a portion of said particles have a first binding moiety and a further portion of said particles have a second binding moiety which is capable of binding with said first binding moiety whereby said particles are, or are capable of being, aggregated together, and wherein said sample is treated with said particles under conditions such that a collection of said particles is aggregated around said cell type of interest.

7. A method of detecting a cell type of interest present or potentially present in a sample comprising treating the sample, in vitro or ex vivo, with lipid vesicle particles which specifically bind to said cell type of interest, said particles having at least one layer of enveloping lipids and incorporating a cytolytic peptide, which is non-covalently attached thereto, wherein the peptide, in response to a predetermined extracellular metabolic signal from the cell type of interest, if present in the sample, interacts with the layer to act as or mediate the opening of pores or channels within the lipid layer to thereby modulate the permeability of the particles, said particles further incorporating a species which is released on said modulation of permeability, wherein said species produces a detectable signal in the presence of said metabolic signal, and monitoring directly or indirectly for the species, wherein said cell type of interest is a bacterium.

8. The method according to claim 7 wherein said metabolic signal comprises a change in pH.

9. The method according to claim 7 wherein said sample is water.

10. The method according to claim 7 wherein said sample is a foodstuff.

11. The method according to claim 7, wherein the cytolytic peptide comprises an integral protein of the lipid layer.

12. The method according to claim 7, wherein the cytolytic peptide spans the lipid layer.

13. The method according to claim 7, wherein the cytolytic peptide is non-covalently attached to an outer lipid layer.

14. The method according to claim 7, wherein the particles comprise a binding agent capable of binding a particle to the cell type of interest when the particle is targeted thereto.

15. The method according to claim 14, wherein the binding agent is an antibody for binding to an antigen on the cell type of interest.

16. The method according to claim 7, wherein the cytolytic peptide is selected from the group consisting of GALA, Helical erythrocyte lysing peptide (HELP), KALA, and LAGA.

17. The method according to claim 7, wherein the cytolytic peptide is N, Myristic-GALA.

18. The method according to claim 7, wherein the cytolytic peptide is selected from the group consisting of Amphotericin B, Alamethicin, Gramicidin, Melittin, Nigericin, P25, Polymixin B, Valinomycin, and Vibriolsin.

19. The method according to claim 7, wherein the species is a dye.

20. The method according to claim 7, wherein the species is an enzyme.

21. The method according to claim 20, wherein the enzyme is alkaline phosphatase, β-Galactosidase or asparaginase, or glucose oxidase.

22. The method according to claim 7, wherein the species is a co-factor or substrate for an enzyme.

23. The method according to claim 7, wherein the metabolic signal comprises a change in ion concentration.

24. The method according to claim 23, wherein the ion is $H^+$, $Na^+$, $Cl^-$, $HCO^-$, or $K^+$.

25. The method according to claim 8, wherein the metabolic signal comprises a change in pH, wherein the pH is above 6.

26. The method according to claim 8, wherein the metabolic signal comprises a change in pH, wherein the pH is above 7.

27. The method according to claim 7, wherein the metabolic signal comprises a change in gas concentration.

28. The method according to claim 7, wherein the metabolic signal comprises a change in carbon dioxide concentration.

29. A method of detecting a cell type of interest present or potentially present in a sample comprising treating the sample, in vitro or ex vivo, with lipid vesicle particles which specifically bind to said cell type of interest, said particles having at least one layer of enveloping lipids and incorporating a cytolytic peptide, which is non-covalently attached thereto, wherein the peptide, in response to a predetermined extracellular metabolic signal from the cell type of interest, if present in the sample, interacts with the layer to act as or mediate the opening of pores or channels within the lipid layer to thereby modulate the permeability of the particles, said particles further incorporating a species which is released on said modulation of permeability, wherein said species produces a detectable signal in the presence of said metabolic signal, and monitoring directly or indirectly for the species, wherein said cell type of interest is a pathogenic cell.

30. The method according to claim 29 wherein said metabolic signal comprises a change in pH.

31. The method according to claim 29 wherein said sample is water.

32. The method according to claim 29 wherein said sample is a foodstuff.

* * * * *